United States Patent [19]
Greenstadt et al.

[11] Patent Number: 6,055,997
[45] Date of Patent: May 2, 2000

[54] ASSISTIVE STEP-OVER CANE ASSEMBLY

[76] Inventors: Lisa Greenstadt; Eugene Greenstadt, both of 16700 Bajio Ct., Encino, Calif. 94136

[21] Appl. No.: 08/847,149

[22] Filed: Apr. 21, 1997

[51] Int. Cl.⁷ ........................................ A61H 3/00
[52] U.S. Cl. ............................. 135/65; 135/66; 135/67; 135/69; 135/911
[58] Field of Search .................. 135/65–67, 69, 135/72, 74, 911; 297/4–6, DIG. 4, 195.11; 403/65, 103, 84

[56] References Cited

U.S. PATENT DOCUMENTS

| | | | |
|---|---|---|---|
| 3,272,210 | 9/1966 | Boruvka | 135/69 X |
| 4,274,430 | 6/1981 | Schaaf et al. | 135/69 X |
| 4,358,138 | 11/1982 | Laughlin et al. | 135/66 X |
| 4,387,891 | 6/1983 | Knochel | 135/67 X |
| 4,641,882 | 2/1987 | Young | 297/4 X |
| 4,722,356 | 2/1988 | Rehder | 135/67 |
| 4,884,587 | 12/1989 | Mungons | 135/74 X |
| 4,890,853 | 1/1990 | Olson | 297/DIG. 4 |
| 5,409,028 | 4/1995 | Lee | 135/66 |
| 5,499,645 | 3/1996 | Baliga | 135/67 |
| 5,524,657 | 6/1996 | Jih | 135/67 X |
| 5,603,517 | 2/1997 | Lorman | 135/67 X |

FOREIGN PATENT DOCUMENTS

| | | | |
|---|---|---|---|
| 61103 | 3/1892 | Germany | 135/68 |
| 1811835 | 4/1993 | Russian Federation | 135/67 |

Primary Examiner—Carl D. Friedman
Assistant Examiner—Winnie S. Yip
Attorney, Agent, or Firm—Robert M. Sperry

[57] ABSTRACT

A step-over cane assembly for facilitating ambulatory movement of users afflicted with certain conditions, such as Parkinson's disease, is disclosed herein. The cane assembly includes an elongate cane member with a tip end and a handle end, the tip end being disposed to contact a walking surface and the handle end providing a grip area to a user. A step-over member is coupled to a lower portion of the elongate cane member proximate the tip end, the step-over member inducing the user to take walking steps when deployed transverse to the elongate member. The step-over member may be rotatably coupled to the elongate cane member, thereby allowing the step-over member to be deployed in an extended position transverse to the elongate member and in a retracted position substantially parallel to the elongate member. When deployed in the extended position, the step-over member serves as a walking obstacle to Parkinson's users of the cane. Encountering this obstacle induces the feet of such a user, which tend to become incapable of movement during certain "off periods", to step over the obstacle and thereby enable forward walking. The step-over member will typically be fabricated using a flexible and durable plastic, which lessens the chance that a user may inadvertently trip and allows such member to be resistant to damage if stepped upon. A miniature flashlight or a phosphorescent material can be applied to a small section of the step-over member so as to increase nocturnal visibility.

14 Claims, 10 Drawing Sheets

BROKEN LINES INDICATE
FLEXIBILITY OF THE WAND (22)

ASSISTIVE STEP-OVER CANE ASSEMBLY

BACKGROUND OF THE INVENTION

1. Field of the Invention

The present invention relates generally to the field of ambulatory assistance devices, and more particularly to assistive walking devices.

2. Description of the Related Art

Parkinson's disease is a degenerative neurological condition which exhibits a variety of symptoms including loss of motor control of hands and legs. Patients experience rigidity, tremors, and inability to walk. Medication is effective for the first 5 to 10 years, at which time the patient will typically experience both hyper-reaction and lack of responsiveness to the medication.

During their 'off' periods (generally occurring several times a day) for maybe an hour at a time, Parkinson's patients are unresponsive to medication and look and feel as if their feet are stuck to the floor, as if frozen. During such times it is impossible to move such patients by the normal walking reflexes common to the unafflicted.

The difficulty in movement experienced by Parkinson's patients during such "off" periods is exacerbated by haste or anxiety. However, there is a way of "tricking" the patient's brain into moving forward by asking the patient to step over an obstacle placed in front of her. For example, the patient's caregiver may place his own foot in front of the patient, and then asks the patient to step over this obstacle. In response, the patient is able to lift her foot higher than the obstacle and place it beyond the other side of the obstacle, thereby having inadvertently taken a stride forward.

The process can be repeated by caretaker and patient until a destination is reached, obviously at considerable inconvenience if undertaken routinely in daily life. Neurologists specializing in the care of Parkinson patients often ask the patients to step over their extended foot to get them to move along. In addition, it is well known that Parkinsonians can overcome their freezing and walk when periodic designs occur along their pathway or objects are left at repeated intervals along their path.

Such specific environmental manipulations have involved placing design patterns on the floor, such as evenly spaced strips of colorful tape, or pieces of garden hose set out in an orderly pattern along a pathway or the extended foot of the neurologist or of the care taker. All of these environmental obstacles or manipulations require dependence on somebody else to assist the patient and are therefore limited in scope and location.

Although a number of techniques have been developed in an effort to address the walking needs of patients with various ambulatory difficulties, none address the aforementioned need for a device suitable for Parkinsonians. For example, U.S. Pat. No. 5,188,138 describes a cane with a hinged cross member, to which is added a pair wheels and associated brakes to enable the user maintain controlled speed. In U.S. Pat. No. 5,351,704, there is described a transparent cane having a built-in lighting device for illuminating the foot path.

Literature published by, for example, The American Parkinson's Disease Association (APDA), the United Parkinson's Foundation (UPF), the National Parkinson's Foundation (NPF), does not appear to yield any information relating to walking devices specially adapted to meet the needs of Parkinsonians.

Accordingly, a need in the art exists for a technique for aiding Parkinsonians in walking which does not require the caretaker to always be adjacent or even available each time the patient has a need to walk. It would also be desirable that such a technique not be reliant upon use of someone else's body part for the obstacle, or rely upon a sequence of fixed obstructions or "markers" along a planned path. There are other patients with neurological damage, such as Multiple Sclerosis (MS) who exhibit movement anomalies at times similar to Parkinsonians, who could also benefit from such a technique.

SUMMARY OF THE INVENTION

The portable step-over cane of the present invention includes a step-over member which serves as a walking obstacle to Parkinson's users of the cane. The patient positions the cane with the step-over member in front of herself, which induces the patient to step over the obstacle. By repeating this process, the patient acquires the ability to move independently.

In a preferred implementation, the step-over cane includes a step-over member, or, equivalently, a "step-over wand", which fits unobtrusively at the lower end of a cane. It is a modern, attractive design. Users will have the option of procuring the step-over wand in isolation and mounting it on their own cane.

The step-over wand may be fabricated out of a flexible and durable plastic. It is of greatest importance to avoid tripping the user and yet resist damage if stepped upon. The step-over wand is made in a bright color visible in dim light, a bright signal- light green, or red, or bright yellow, or orange. A phosphorescent material can be applied to a small section of the step-over wand to increase visibility at night time.

For individuals who are likely to use the step-over cane at night, a small pen flash light will be made available. This is to be mounted, with a pair of plastic or other suitable fasteners, on the upper end of the cane near the handle, where the person can easily reach the "on" switch to illuminate the area of the step-over wand and check the accurate placement of the foot.

The present invention is intended allow a patient to obtain the walking exercise necessary to maintain muscle tone, ambulate from a parking place to a restaurant seat, or stroll through a museum. The step-over cane also enables parkinsonians to independently move during "off" periods to reach required medication, restrooms, and to escape from dangerous conditions such as a fire or the like.

BRIEF DESCRIPTION OF THE DRAWINGS

Additional objects and features of the invention will be more readily apparent from the following detailed description and appended claims when taken in conjunction with the drawings, in which:

DESCRIPTION OF THE PREFERRED EMBODIMENTS

Figure 1:
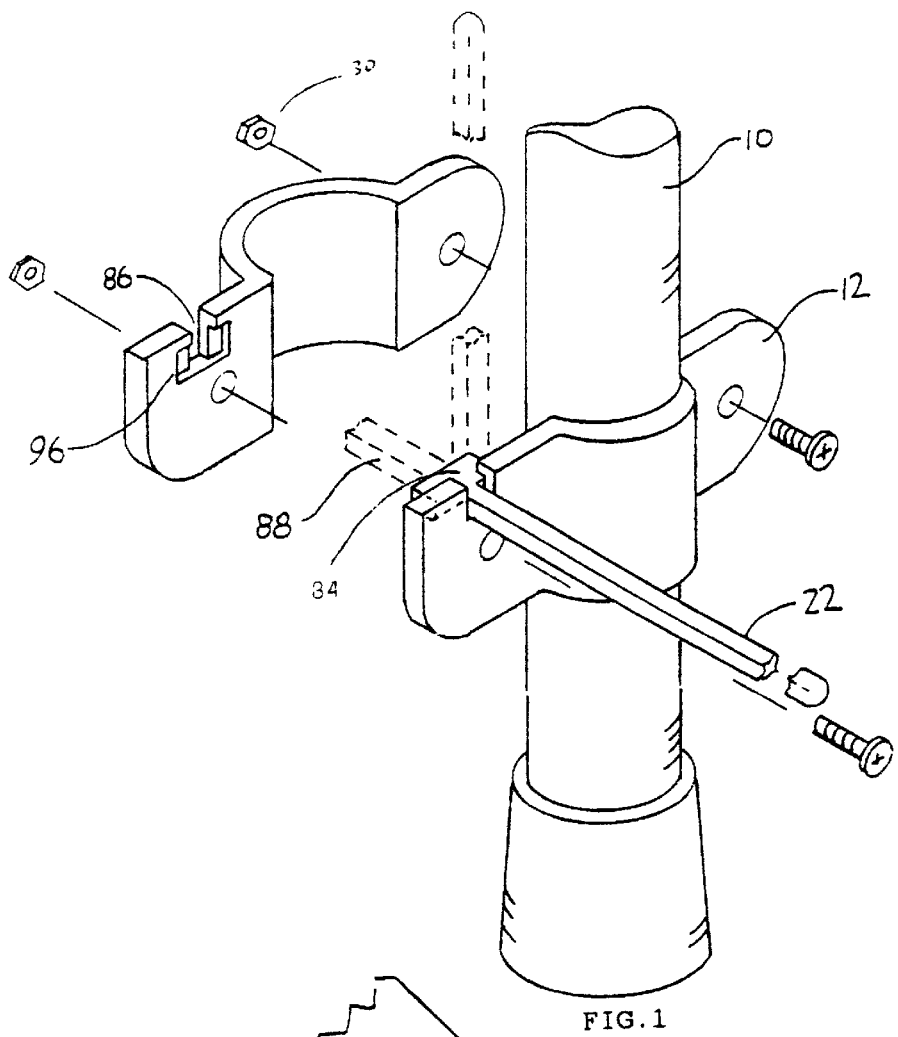
FIG. 1 is a perspective view of a step-over cane member configured with a rectangular block-anchored step-over wand.
Figure 1A:
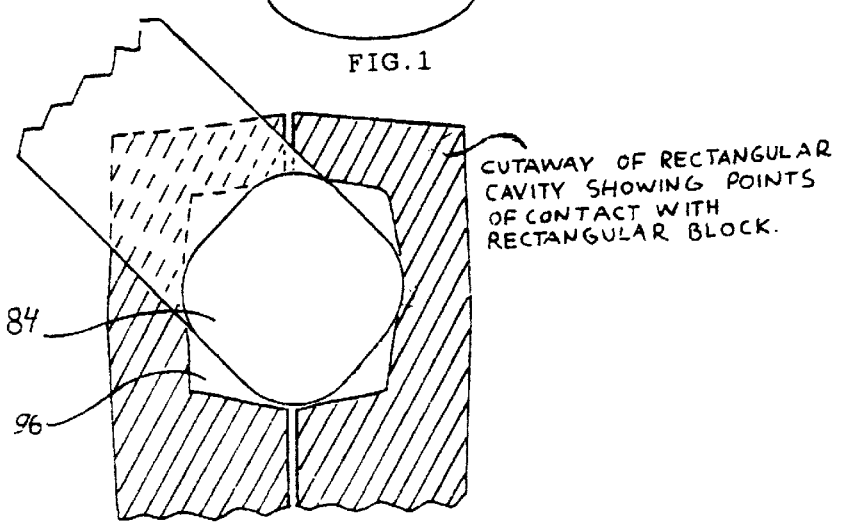

The various embodiments of the step-over cane of the present invention are each intended to satisfy one or more of the following objectives:

1. to supply a portable obstacle, in the form of the step-over wand, to enable individuals with specific movement disorders to walk;

2. to make the step-over wand (i.e., the obstacle) out of a sturdy yet flexible plastic material, although a light weight, stainless steel flexible spring could also be utilized;

3. to make the setting of the step-over wand position easy for parkinson's patients who may exhibit variable degrees of finger movement disorders;

4. to make it possible to store the step-over wand out of the way, against the cane, when no longer in use as an obstacle;

5. to make the step-over wand usable by both left and right-handed people;

6. to provide canes with decorative designs that would appeal to individuals who may be reluctant to walk around with a cane because of prior negative connotations;

7. to make pen lighting, or other types of compact battery-powered lighting, available to facilitate use of the step-over wand at night 8. to enable a step-over member to be conveniently and unobtrusively mounted or clamped to a cane, or walking stick, or assistive walker device.

With regard to the fourth objective above, the ability to retract the step-over wand out of the way from it's horizontal to a vertical position against the cane is believed to be especially beneficial in the case of crowded areas (e.g., in a theater, airplane or similarly confined location) where use of canes and the like could cause annoyance. Accordingly, various mechanisms are described below for converting the step-over cane into a cane of conventional form and function.

Descriptions of five particular designs of the step-over cane are set forth below, followed by a drawing reference numerals worksheet. The term "cane" will be used to signify various walking aids such as canes, walking sticks, crutches, and four-legged metal walker devices.

Rectangular Block-Anchored Step-Over Wand Member

FIG. 1 is a perspective view of a step-over cane configured in accordance with one aspect of the present invention. The step-over cane includes a longitudinal cane 10, to which is mounted a step-over member hereinafter referred to as step-over wand 22. It should be understood that in alternate implementations of the present invention, the step-over wand may be mounted on a walking stick, assistive walker, or crutch, instead of on the cane 10. FIG. 1 also shows a detailed view of the manner in which the wand 22 fits within a clamp 12. Said clamp 12 is made entirely of sturdy plastic material except for two metal bolts and hexagonal nuts 30. The forward section of the clamp houses the step-over wand. The wand may be fabricated from a piece of pliable plastic, having a short section and a long section. The short section, or horizontal base, of the wand consists of a small rectangular block of dimensions approximately ⅜" in length and 3/16" in thickness. Said rectangular block 84 is housed within a slightly larger hollow, rectangular cavity 96, in the forward projection of the clamp. Said block is intended to stabilize the wand 22 within the housing provided by the clamp 12. The long section of the wand projects perpendicular to the short section formed by the rectangular block. This long section is approximately 6" in length and ⅛" in thickness and extends outside the clamp to form the step-over obstacle (wand). The outside section of the wand 22 exits the clamp through a snug opening in the form of a slot 86, which allows the wand to be rotated over a 180° radius from the left-of-cane horizontal position to the right-of-cane horizontal position. As the wand is rotated over the 180°, the corners of the rectangular block are pressed against the sides of the rectangular block cavity to provide an adequate amount of resistance to maintain the wand in any one of its three desired orientations of left, right, or upward (resting).

Figure 2:
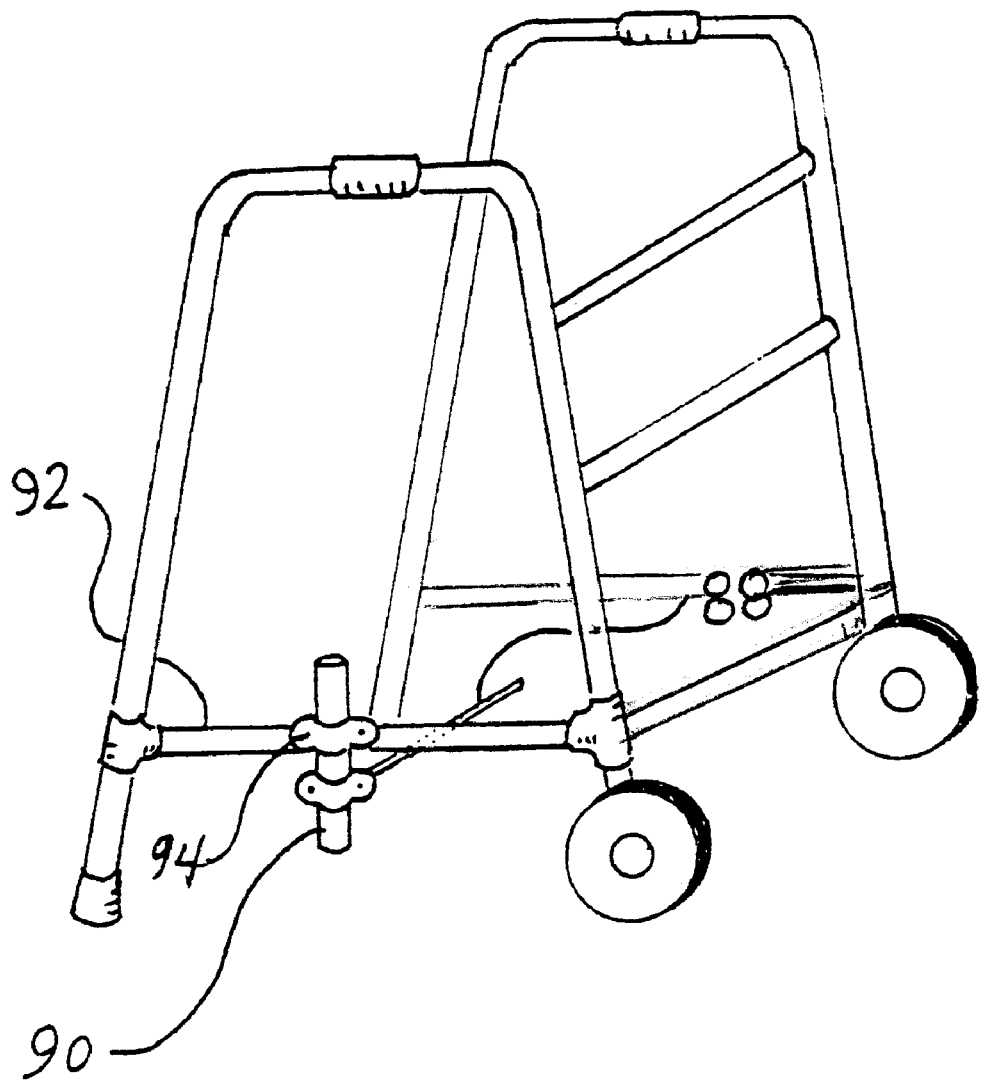
FIG. 2 is a perspective view demonstrating the ease of application of the step-over wand to the supporting elongate members of an assistive walker device.

FIG. 2 is a perspective view of a walker device with a cross-bar 92 added between the forward and the rear legs on the right side of the walker. This is intended to provide support for a short cane segment (or cane like rod) 90 on which the step-over wand assembly is mounted. A ¾" bracket and two rivets 94, one on each side of said segment 90, hold the segment 90, together with its attached step-over wand assembly, to the cross-bar 92 to keep it firmly in place.

Clamp-Mounted Two-Positions Step-Over Wand

Figure 3:
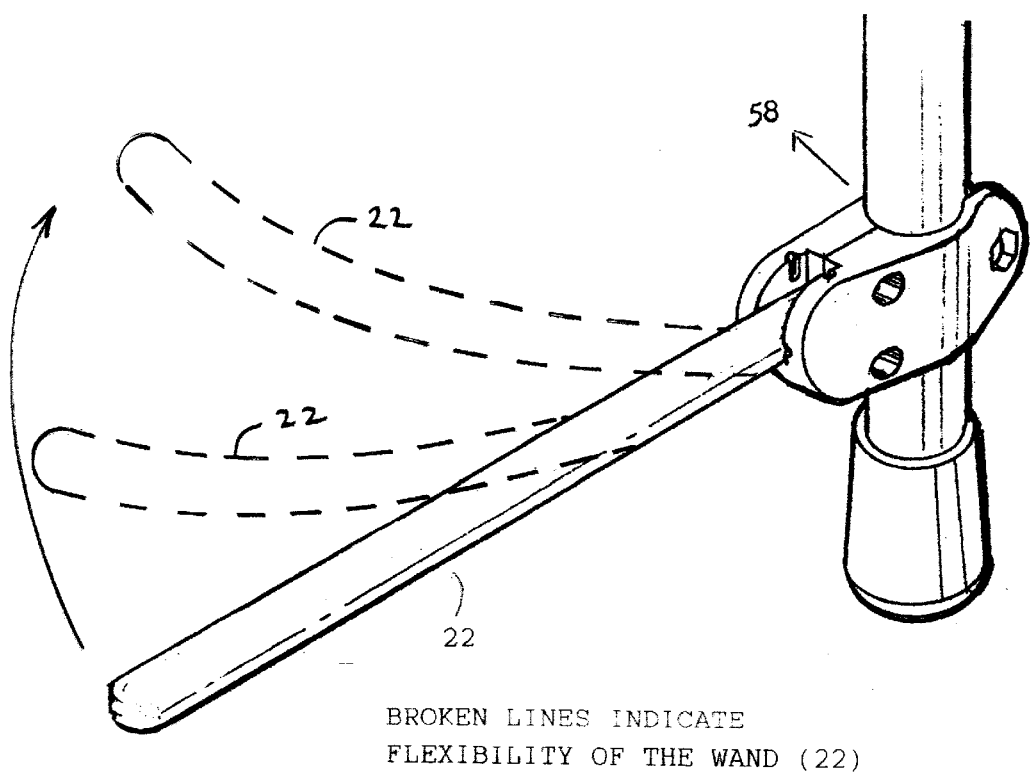
FIG. 3 is a perspective view of a step-over cane of the present invention configured with a clamp-mounted two-position step-over wand.
Figure 4:
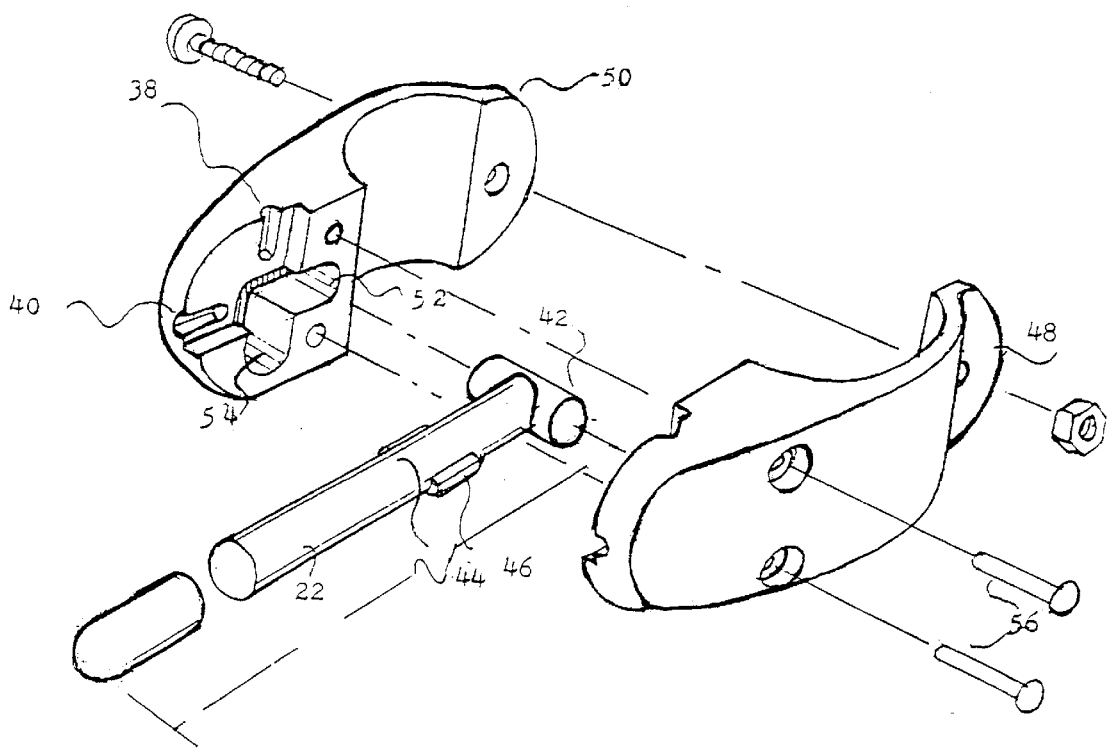
FIG. 4 is a partially disassembled view of the clamp assembly of the step-over cane of FIG. 3.

A perspective view of an alternate implementation of the step-over cane is provided in FIG. 3. The step-over wand 22 is held in place by a clamp mounted on a walking cane, at approximately two inches from floor level. The entire clamp assembly is made of molded plastic, except for two rivets and one "8-32" screw and nut. The clamp provides the housing and control for the wand 22. The step-over wand 22, as seen in FIG. 4, is attached to the pivot rod 42. FIG. 4 shows the rear left and right clamp parts 48,50. The rear portion of the clamp is the section that wraps around the cane. The tightness of the fit around the cane can be adjusted by turning the 8-32 screw. The front of the clamp is secured against any disturbance of the function of the step-over wand 22 by the use of two permanently set tubular rivets 56. The front of the clamp defines the cavities which hold the pivot rod 42 of the wand in the desired position. Cavity A 52, together with its other half inside the opposite half of the clamp, holds the pivot rod 42 in the horizontal position and cavity B 54, together with its other half inside the opposite half of the clamp, holds the pivot rod in the vertical position, out of the user's way, and snug against the leg of the cane. Two locking keys 44,46 are molded to the sides of the step-over wand 22 to prevent accidental dislodging of the step-over wand from its desired position. Grooves 38,40, with corresponding grooves inside the opposite half of the clamp, are provided to house the locking keys 44,46.

In the implementation of FIGS. 3 and 4, the step-over wand 22 is placed in its vertical position by grasping it and pulling the wand 22 horizontally so as to free the locking keys from their grooves, then swinging the wand 22 to its vertical position. When the step-over wand 22 is placed in it's vertical position, all the user needs to do is to let it fall into its cavity A, and give it a gentle push to make sure that the locking keys along side the wand have descended into their grooves. In this way the locking keys will be held in place until the user again desires to place the cane in its horizontal position. At such time, the user pulls the step-over wand 22 up from its locking position so that it is now free to swing to its horizontal position. A gentle push inward will now lock the locking keys in the appropriate groove. These will hold the step-over wand 22 securely against the possible dislodging by an accidental kick of the user's foot. The clamp assembly will preferably be placed with the step-over wand 22 on the right side of the cane if the user is left-handed so that the step-over wand 22 will extend horizontally in front of the left foot. In order to alternately adapt the cane for use by left-handed and right-handed persons, the clamp is simply rotated by 180 degrees about the longitudinal axis of the cane.

Again, the step-over wand 22 provides an horizontal obstacle designed to cause a user of the step-over cane to inadvertently take a walking step forward when confronted thereby. The wand 22 is formed of material, such as rubber, thin plastic or metal wire or the like, which is self-supporting, yet readily flexible. Thus, when the user moves his foot forward, in taking a step, his foot will contact the wand 22. If his foot is raised, as in a normal step, the wand 22 will flex, as seen in dotted lines in FIG. 3, so as not to interfere with movement of the foot. On the other hand, if the user is shuffling, without raising his foot, wand 22 will gently tap the user's ankle to remind the user to raise his foot and, thereafter, will flex to prevent interfering with the movement of the foot.

Step-Over Wand Positioned Using Adjustable Wing Nut

Figure 5:
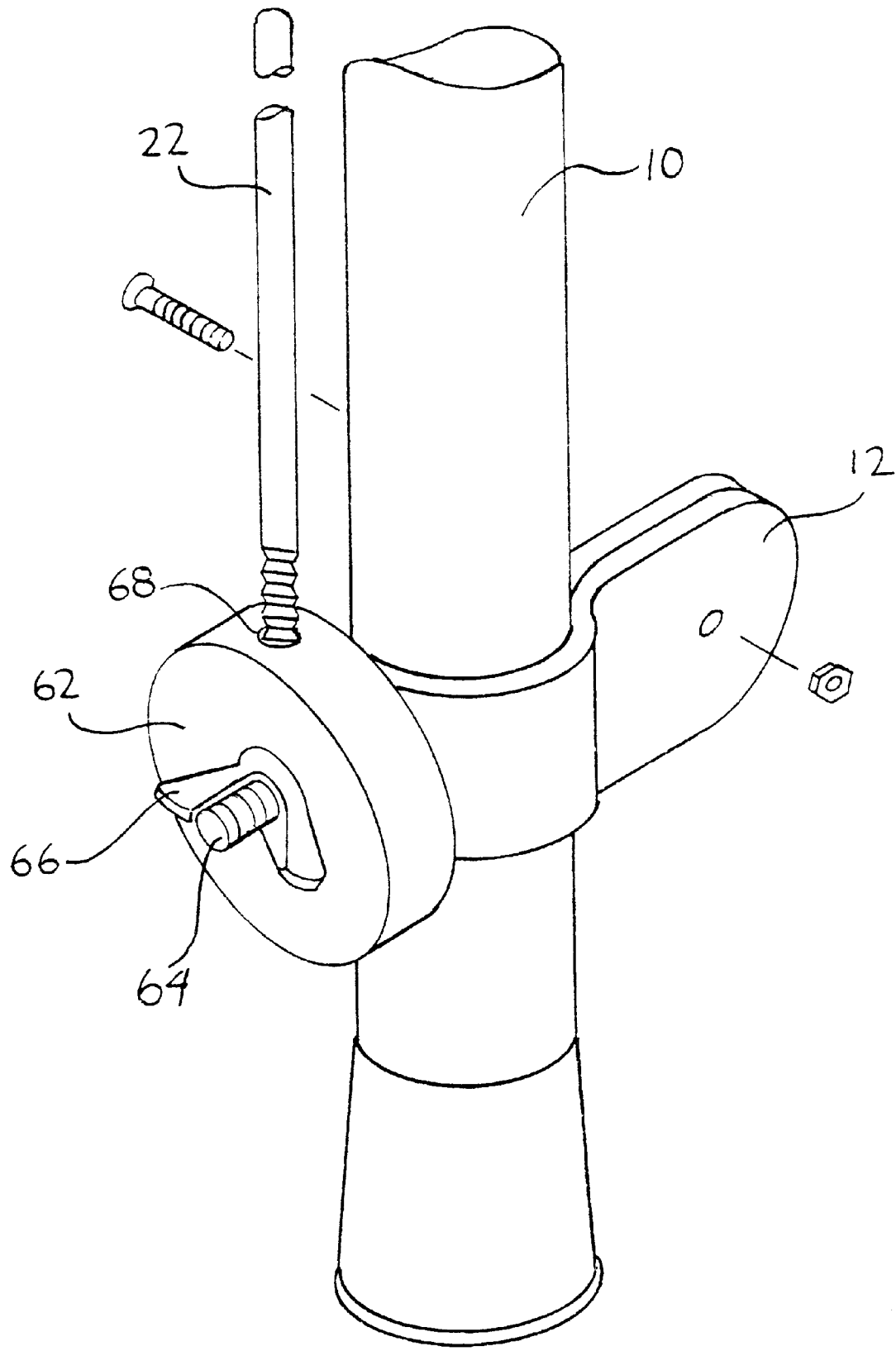
FIG. 5 is a perspective view of a step-over cane of the present invention in which the step-over wand is adjustably positioned by tightening the wing nut.

The following paragraphs describe the design and function of the step-over wand illustratively represented in FIG. 5. A molded plastic clamp 12 is fastened securely to the cane, approximately two inches above floor level, just above the rubber tip of the cane. The ¾ inch clamp 12 holds the step-over wand rotation wheel 62 in place by using a 1 inch bolt 64 which passes through the whole in the front portion of the clamp. and then through the center whole of the rotation wheel. The position of the wheel 62 is maintained by tightening the wing nut 66 to achieve the desired orientation of the step-over wand 22. The step-over wand 22 is screwed into the side of the wheel by threads 68.

A right-handed person will set the horizontal step-over wand 22 on the left side of the cane. A left-handed person will set the step-over wand 22 on the right side of the cane. That is, the cane may be alternately adapted for use by left-handed and right-handed persons by simply changing the position of the wand by loosening and then tightening the wing nut to achieve the desired orientation of the wand. When the step-over wand 22 is no longer needed, it may be retracted to a vertical orientation parallel to the longitudinal axis of the cane. The advantage of this design is that a person accustomed to perform mechanical tasks may succeed in putting all necessary parts together by herself or himself.

Levered-Rod Step-Over Wand

Figure 6:
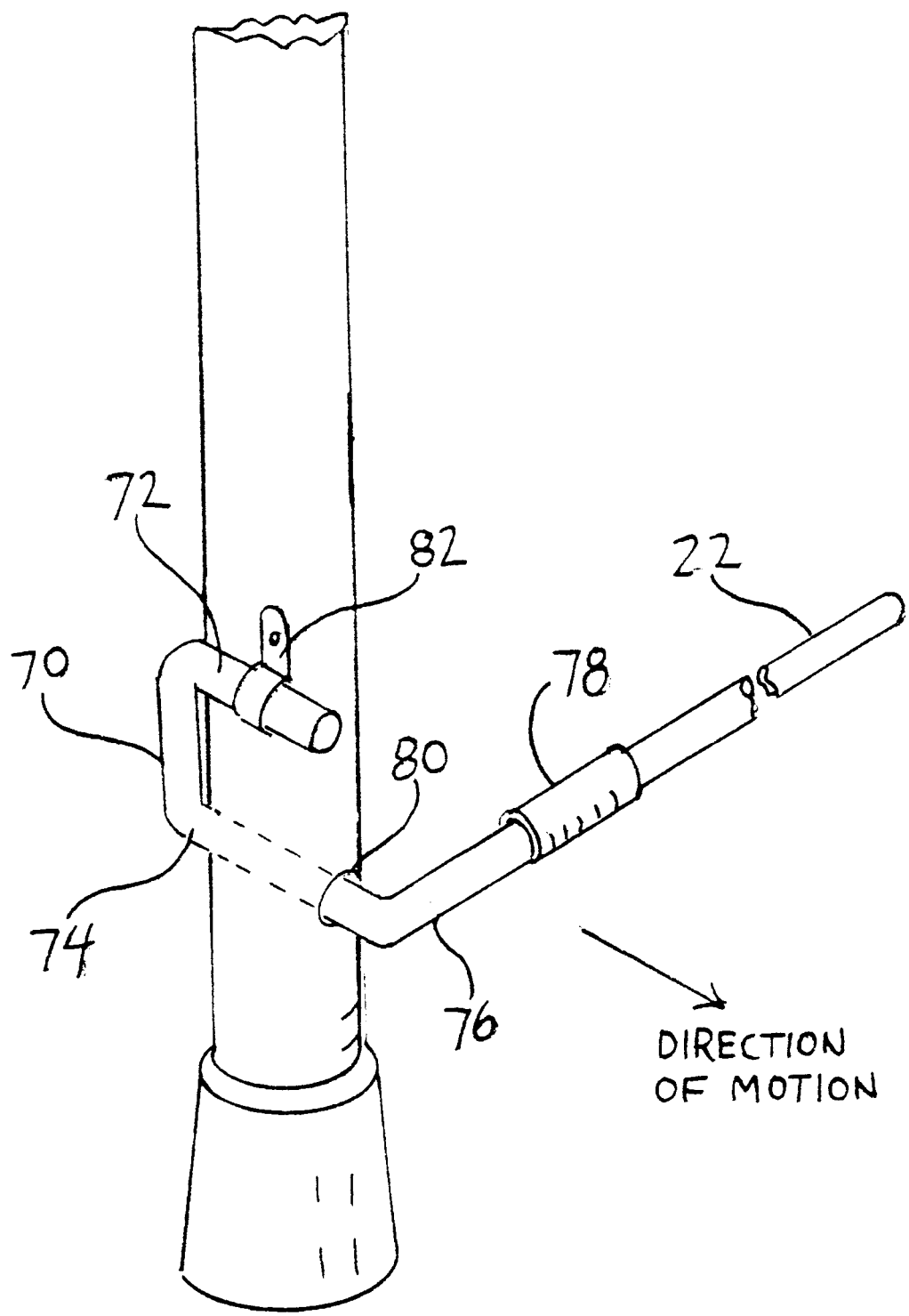
FIG. 6 depicts an implementation of a the step-over wand incorporating a levered-rod application of a step-over wand assembly.

The implementation of the step-over cane shown in FIG. 6 makes use of a 3/16 inch steel rod to hold the step-over wand in the desired position. In a preferred implementation the steel rod is 5 inches long, and is bent at a 90 degree angles at the one inch position (A segment) 72, and again at the two inch position (B segment) 74. The remaining 3 inch section, C segment 76, is passed through the body of the cane via a hole between the back and front of the cane. The 3/16 inch hole may be painted in the same manner as the rest of the cane, for protection of the exposed wood. The hole is typically placed 2 inches above floor level. The A & B segments 72, 74 are placed on the right side of the cane (from the perspective of the user of the cane) to act as levers for raising and lowering the step-over wand 22.

Approximately 2 inches of the rod (C segment) 76 emerges in the front of the cane. This C segment is now bent to the left of the cane (again from the perspective of the user of the cane) for right-handed users and to the right of the cane for left-handed users. The end of the rod is then connected to the step-over wand by way of a coupling nut 78, which is threaded to accept both the rod and the step-over wand 22.

The advantages of this design reside in its simplicity of manufacture and its sturdiness. It would serve well as a step-over cane for an outdoor person who likes the wilderness and would be inclined to climb rocky trails or sandy dunes. For esthetic considerations exposed portions of the steel rod 76 are preferably covered with black shrink tubing to match the black color of the cane. A protective black plastic tip may also be placed at the exposed end of the steel lever. The lever is held in place by a plastic hook 82 to prevent possible dislodging of the step-over wand 22 by an inadvertent kick to the step-over wand 22.

Night Time Illumination of the Wand

Figure 7:
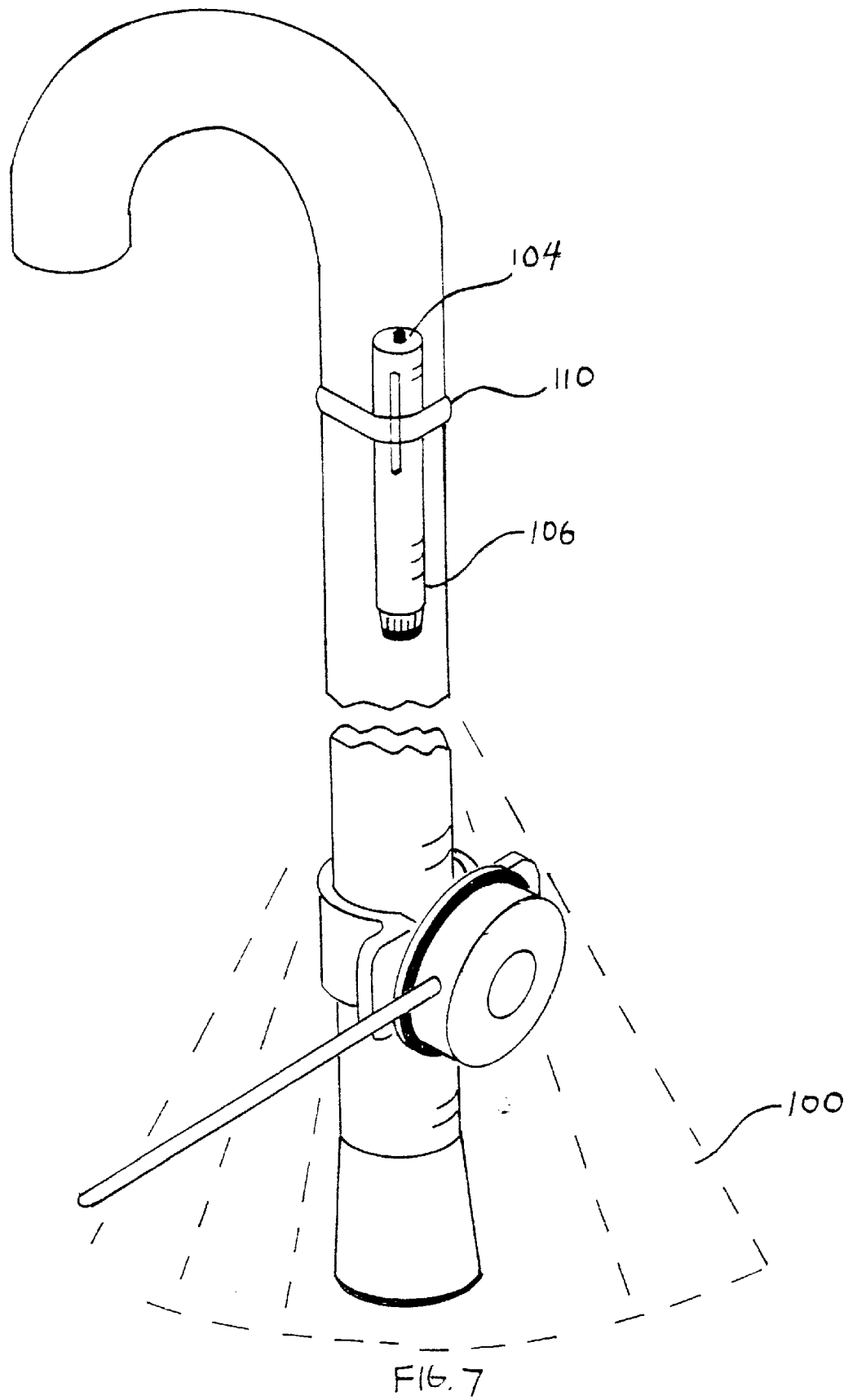
FIG. 7 illustratively represents an implementation of the step-over cane in which the step-over wand is illuminated by a pen flashlight.
Figure 8:
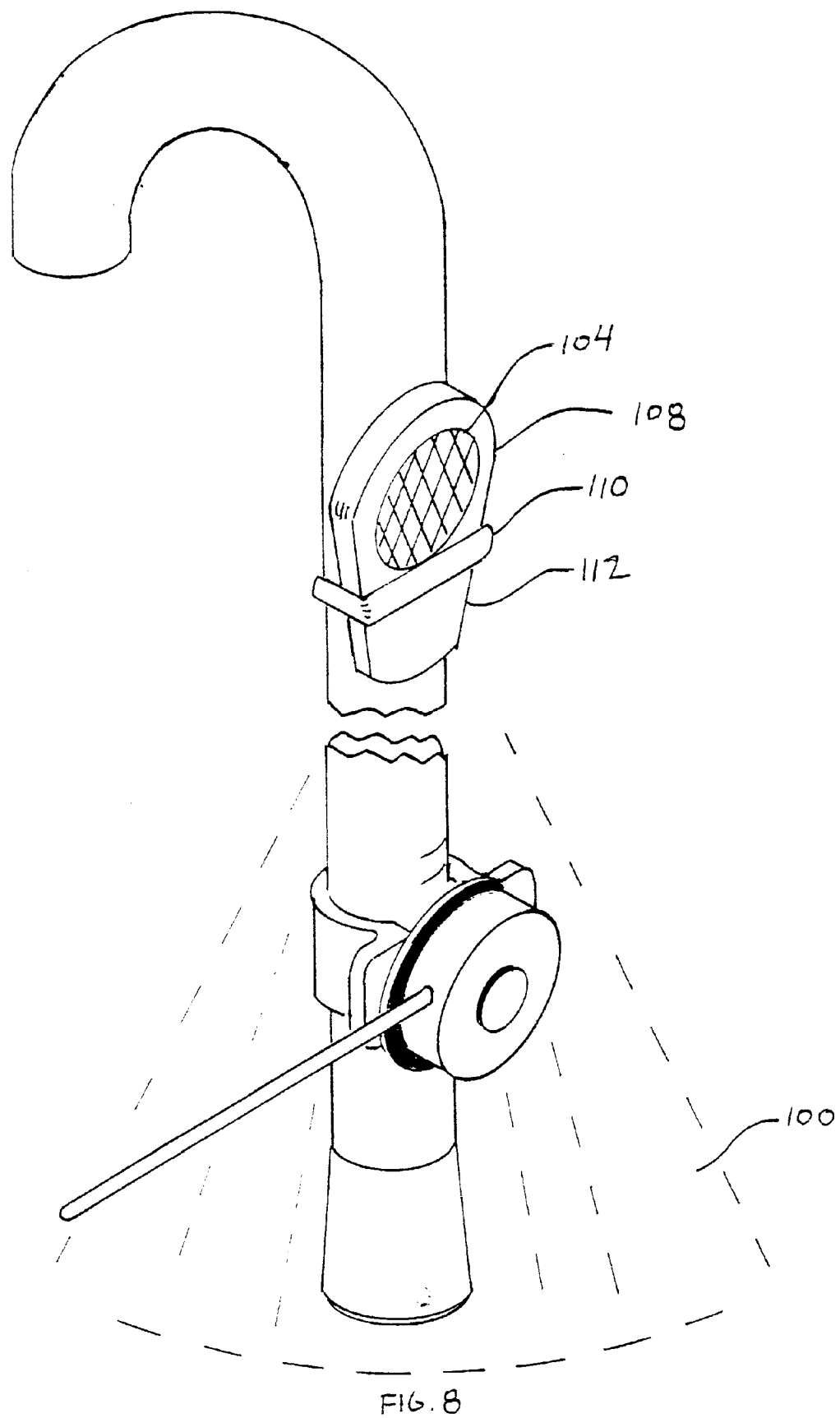
FIG. 8 illustratively represents an implementation of the step-over cane in which the step-over wand is illuminated by a miniature key flashlight.

FIGS. 7 and 8 illustratively represent implementations of the step-over cane in which the step-over wand 22 is illuminated by a pen light 106 and by a key light 108, respectively. In the implementation of FIG. 7, the pen light is held by a thin plastic clamp 104 such that the longitudinal axes of the pen light 106 and cane member 10 are substantially parallel. The pen light 106 includes an on-switch 104 and an illuminating end 100. In FIG. 8, an elastic band 110 is employed to secure the key light 108 to cane member 10. In both FIGS. 7 and 8, the step-over wand 22 is preferably coupled to cane member 10 using a rectangular block-anchored step-over wand assembly substantially similar to that described above with reference to FIGS. 1 and 2.

Hub-Mounted Step-Over Wand

Figure 9:
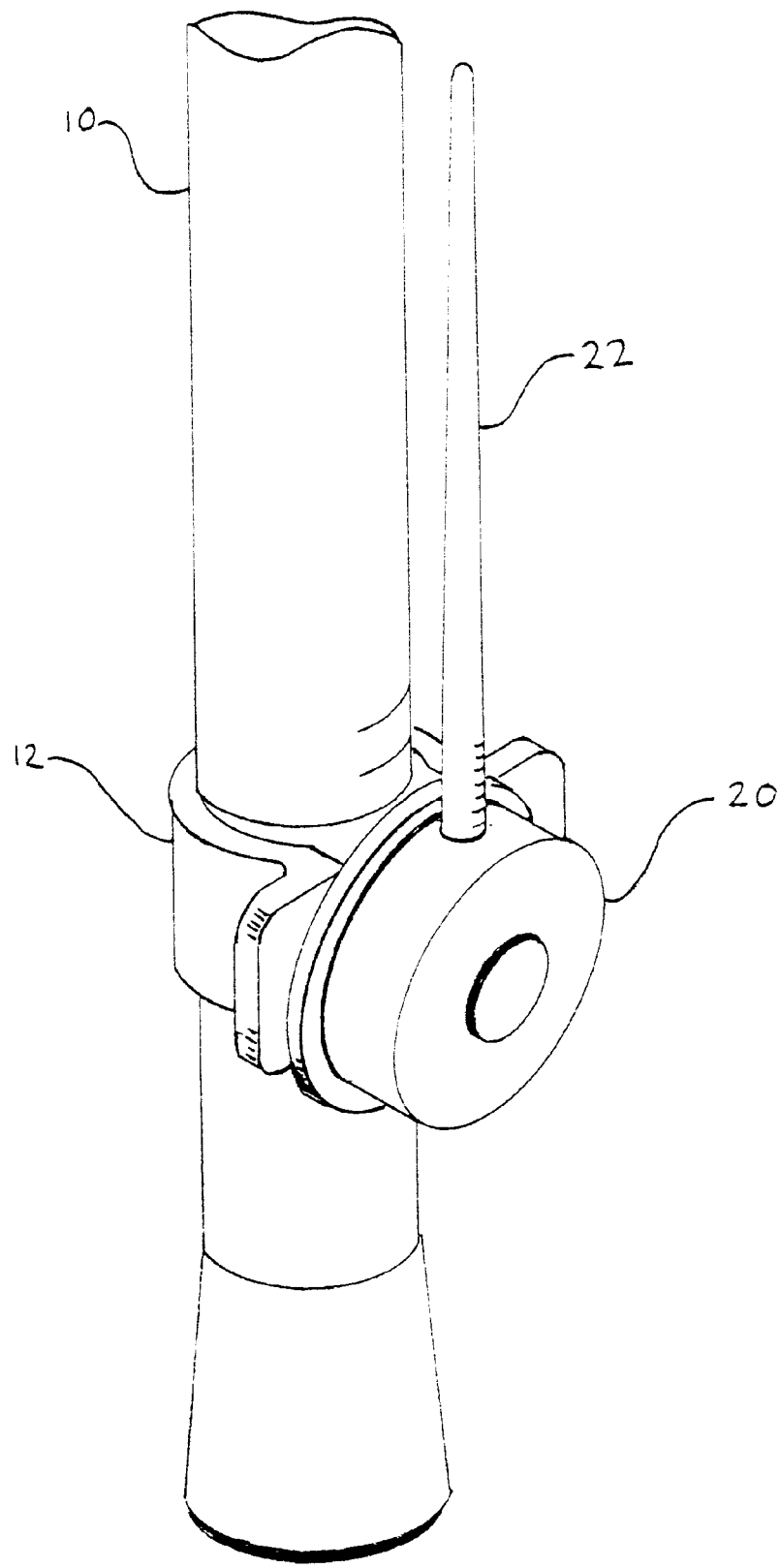
FIG. 9 is a perspective view of a step-over cane of the present invention configured with a hub-mounted step-over wand.
Figure 10:
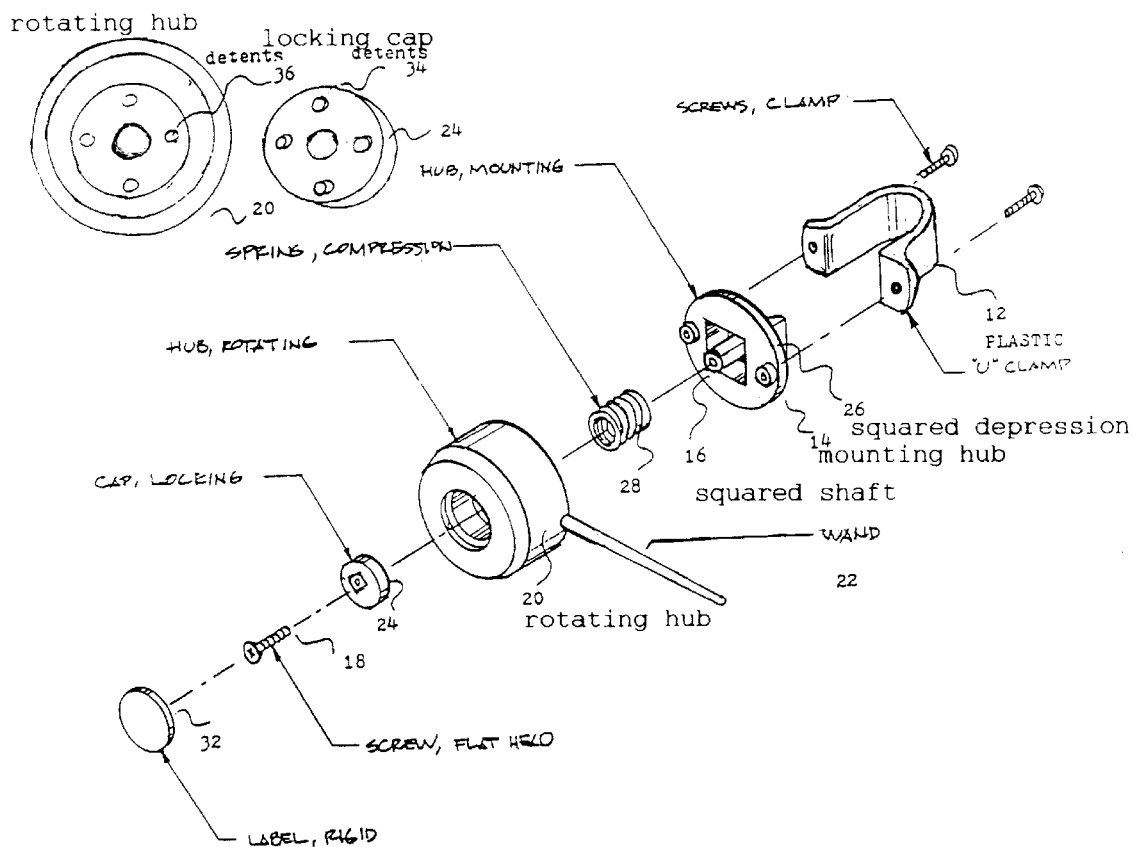
FIG. 10 is a partially disassembled view of the step-over wand of FIG. 9.

FIG. 10 provides a partially disassembled view of the step-over cane of FIG. 9. As is indicated by FIGS. 9 and 10, the step-over cane includes a plastic clamp 12, which is tightened around the cane by two screws connecting it to a mounting hub 14. The mounting hub 14 has a squared shaft 16 in its center, which surrounds a flat head screw 18 holding the entire assembly together. The squared shaft 16 is elevated just enough to keep the locking cap 24 from turning from its fixed position. A squared depression 26 occupies the center of mounting hub 14, and this depression 26 houses a compression spring 28 holding the rotating hub 20 in contact with a locking cap 24. The rotating hub 20 holds the plastic step-over wand 22. In addition, the locking cap 24 and the rotating hub 20 are equipped with detents that lock the position of the step-over wand 22 in anyone of three orientations: Left, center (vertically out of the way), or right.

A significant advantage of the design represented by FIG. 9 is that ready access is provided to both left and right handed users. To change the orientation of the step-over wand 22, a user simply pushes the rotating hub 20 toward the cane and turns it to the desired position of the step-over wand 22. The entire assembly is capped by a small, rigid plastic plate inscribed with a trade name or the like. The assembled components are shown in perspective in FIG. 9.

The previous description of the preferred embodiments is provided to enable any person skilled in the art to make or use the present invention The various modifications to these embodiments will be readily apparent to those skilled in the art, and the generic principles defined herein may be applied to other embodiments without the use of inventive faculty.

Thus, the present invention is not intended to be limited to the embodiments shown herein but is to be accorded the widest scope consistent with the principles and novel features disclosed herein.

What is claimed is:

1. A walking assistance device comprising:

a walking aid, a projecting member formed of material which is self-supporting yet readily flexible coupling and extending outwardly from a walking aid in a direction substantially perpendicular to the walking aid whereby said projecting member of said walking aid will project into the path of movement of the user's foot to gently tap the user's ankle if the user's foot is not raised in a normal walking manner and to flex, upon continued movement of the foot to prevent interfering with movement of the user's foot.

2. The device of claim 1 wherein:

said walking aid is a cane.

3. The device of claim 1 wherein:

said walking aid is a walker.

4. The device of claim 1 wherein:

said projecting member is formed of plastic.

5. The device of claim 1 wherein:

said projecting member extends to a position where it can engage at least one of the user's feet as the user walks.

6. The device of claim 1 wherein: said projecting member provides visual and tactile signals to the user.

7. The device of claim 1 wherein: said projecting member is brightly colored.

8. The device of claim 1 wherein: said projecting member is releasably attached to said walking aid.

9. The device of claim 1 wherein: said projecting member is movable to a position lying substantially parallel to said walking aid.

10. The device of claim 1 wherein: said projecting member is hingedly attached to said walking aid.

11. The device of claim 1 further comprising:

means carried by said walking aid for illuminating said projecting member.

12. The device of claim 1 wherein:

said projecting device is phosphorscent.

13. The device of claim 1 wherein:

said projecting member glows in the dark.

14. The device of claim 1 wherein:

a said projecting member extends from said walking aid at a level substantially equal to that of the user's ankle.

* * * * *